United States Patent [19]

Lipsky

[11] Patent Number: 5,496,355
[45] Date of Patent: Mar. 5, 1996

[54] EXTRAOCULAR MUSCLE SENSOR AND STIMULATOR

[76] Inventor: Stephen N. Lipsky, 1161 York Ave. Apt., 9N, New York, N.Y. 10021

[21] Appl. No.: 342,592

[22] Filed: Nov. 21, 1994

[51] Int. Cl.$^6$ .................................................... A61N 1/36
[52] U.S. Cl. ............................................................... 607/53
[58] Field of Search ................................... 607/53, 54, 48

[56] References Cited

U.S. PATENT DOCUMENTS 5,109,844  5/1992  de Juan et al. .......................... 607/53
5,360,438  11/1994  Fisher ...................................... 607/53

Primary Examiner—William E. Kamm
Assistant Examiner—Scott M. Getzow
Attorney, Agent, or Firm—Lyon & Lyon

[57] ABSTRACT

A method and apparatus for reactivating a paralyzed or non-inervated lateral rectus muscle of the eye. The paralyzed lateral rectus muscle is reactivated by providing a stimulation signal of equal magnitude and frequency of neuronal impulses received by the contralateral medial rectus muscle and detected by an electrode installed therein. The stimulation signal is provided to the paralyzed lateral rectus muscle by way of an electrode installed therein. Control circuitry operates such that the stimulation signal will only be provided to the paralyzed lateral rectus muscle when neuronal impulses are being received by the contralateral medial rectus muscle but not the ipsilateral medial rectus muscle alone and not simultaneously with the ipsilateral medial rectus. The control circuitry will also provide a tonic pulse of predetermined frequency and magnitude to the paralyzed lateral rectus muscle when no neuronal impulses are being sent to the contralateral or ipsilateral medial rectus muscles.

1 Claim, 4 Drawing Sheets

EYEBALL AND INSERTIONS OF THE FOUR RECTI OCULIS
FRONT VIEW

EYEBALL AND INSERTIONS OF THE TWO OBLLIQUE OCULI,
POSTERIOR VIEW

| TABLE 1 NAND 410 ||| TABLE 2 NAND 420 ||| TABLE 3 NAND 430 ||| TABLE 4 NOR 450 |||
|---|---|---|---|---|---|---|---|---|---|---|---|
| IN 1 | IN 2 | OUT 410 | IN 1 | IN 2 | OUT 420 | IN 1 | IN 2 | OUT 430 | IN 1 | IN 2 | OUT 450 |
| 1 | 1 | 0 | 1 | 0 | 1 | 1 | 1 | 0 | 1 | 1 | 0 |
| 1 | 0 | 1 | 1 | 1 | 0 | 0 | 1 | 1 | 1 | 0 | 0 |
| 0 | 1 | 1 | 0 | 1 | 1 | 1 | 1 | 0 | 0 | 1 | 0 |
| 0 | 0 | 1 | 0 | 1 | 1 | 1 | 1 | 0 | 0 | 0 | 0 |

EXTRAOCULAR MUSCLE SENSOR AND STIMULATOR

BACKGROUND OF THE INVENTION

1. Field of the Invention

This invention relates generally to apparatus for stimulating a paralyzed or non-inervated lateral rectus muscle of the eye and more particularly concerns an extraocular muscle sensor and stimulator apparatus and method.

2. Description of the Prior Art

With reference to FIGS. 1 and 2, the basic anatomy of the human eye 10 will be shown. Human eyes 10, known to those skilled in the art as "globes", are coated with tissue known as conjunctiva and Tenon's fascia 20. The cornea 30 covers the iris 40 and the pupil 50. The substance of the eyeball itself is the sclera 60. The optic nerve 70 originates at the back of the globe. The eyes 10 are moved by the extraocular muscles. Each eye has six of these extraocular muscles, the lateral rectus 80, the medial rectus 90, the superior rectus 100, the inferior rectus 110, the inferior oblique 120 and the superior oblique 130.

The extraocular muscles 80, 90, 100, 110, 120 and 130 are controlled by three of the twelve cranial nerves: the third cranial nerve, known to those skilled in the art as "CN III" or the oculomotor nerve, the fourth cranial nerve, known to those skilled in the art as "CN IV" or the trochlear nerve, and the sixth cranial nerve, known to those skilled in the art as "CN VI" or the abducens nerve.

As is well known to those skilled in the art, CN III, the oculomotor nerve, stimulates the superior rectus muscle 100, the medial rectus muscle 90, the inferior rectus muscle 120, and the inferior oblique muscle 120 (shown only in FIG. 2). The superior rectus muscle 100 is responsible for upward rotation of the eye. The medial rectus muscle 90 is responsible for in-turning the eye. The inferior rectus muscle 110 is responsible for downward rotation of the eye. The inferior oblique muscle 120 is responsible for extortional rotation of the eye.

As is also well known to those skilled in the art, CN IV, the trochlear nerve, stimulates the superior oblique muscle (known as SO). The superior oblique muscle 130 is responsible for intortional rotation of the eye. Finally, CN VI, the abducens nerve, stimulates the lateral rectus muscle 80. The lateral rectus muscle 80 is responsible for out turning of the eye.

The sixth cranial nerve often becomes paralyzed in patients during or after neurological diseases such as trauma, stroke, high blood pressure, diabetes, tumors and the like. Also, some patients are born without sixth cranial nerves in a condition known as Duane's Retraction Syndrome. Paralysis of the sixth cranial nerve often causes the sighted patient to suffer from bothersome double vision, or diplopia. Prior art solutions to diplopia involve treatment with prism glasses, complicated surgery, and/or injection of muscle toxins.

None of the prior art treatments, however, provide ideal results. Specticals often do not correct the problem in all fields of gaze. Furthermore, specticals must be adjusted often. Surgery involves movement of a combination of the six extraocular muscles to different positions on the eye. Surgery of this nature is complex, often irreversible, and may not completely relieve the diplopia. Finally, muscle toxin injection involves Botulinum toxin. The effects of toxin injection are unpredictable, may cause further limitation of eye movement and must be repeated up to six times per year.

None of these prior art solutions reactivate the lateral rectus muscle 80, which would provide a true physiologic cure to diplopia. It would therefore be desirable to have a solution for diplopia that reactivates the lateral rectus muscle 80.

As is known to those skilled in the art, it is possible to externally stimulate the lateral rectus muscle in Rhesus monkeys. In general, neural stimulation of any body muscle is accomplished by neuronal impulses and occurs at the junction of the muscle and the nerve that stimulates that muscle. This junction is known as the neuromuscular junction. As is well known, neuronal impulses are of a single amplitude with a variable frequency. As the frequency of pulses to the muscle increases the contraction of the muscle increases in an exponential fashion. It is possible to measure the neuronal impulses to the extraocular muscles using microelectrodes. The prior art has demonstrated that is possible to stimulate a paralyzed muscle. The prior art, however, does not teach or suggest how to integrate the stimuli from other muscles in order to drive a paralyzed muscle.

SUMMARY OF THE INVENTION

The present invention overcomes the problems and disadvantages of the prior art through installation of a first electrode in the ipsilateral lateral rectus muscle (the term "ipsilateral" means "with reference to given point, on the same side", i.e., any structure on the same side of the patient's body as the paralyzed muscle), a second electrode installed in the ipsilateral medial rectus muscle and a third electrode in the contralateral medial rectus muscle (the term "contralateral" means "relating to the opposite side", i.e., any structure on the opposite side of the patient's body as the paralyzed muscle). These electrodes are capable of detecting and/or receiving neuronal impulses received by the muscles in which they are installed. A control unit is installed in the patient that is in electrical communication with the first electrode, the second electrode and the third electrode. The control unit provides a stimulation signal to the first electrode that is of equal magnitude and frequency of neuronal impulses received by the contralateral medial rectus and detected by the third electrode when neuronal impulses are received by said third electrode but not said second electrode. The control unit also provides an electrical impulse of predetermined magnitude and frequency to the first electrode when no neuronal impulses are detected by the second and third electrodes. This arrangement allows the integration of stimuli received by other muscles in order to create signals that drive paralyzed ocular muscles.

The above and other preferred features of the invention, including various novel details of construction and combination of parts, will now be more particularly described with reference to the accompanying drawings and pointed out in the claims. It will be understood that the particular device and method embodying the invention are shown by way of illustration only and not as limitations of the invention. As will be understood by those skilled in the art, the principles and features of this invention may be employed in various and numerous embodiments without departing from the scope of the invention.

BRIEF DESCRIPTION OF THE DRAWINGS

Reference is made to the accompanying drawings in which are shown illustrative embodiments of aspects of the invention, from which novel features and advantages will be apparent.

FIG. 6a shows an embodiment of an electronic circuit for the stimulation unit of the present invention.

FIG. 6b shows truth tables for the logic elements used in logic circuit shown in FIG. 6a.

DETAILED DESCRIPTION OF THE DRAWINGS

Referring now to the figures, the presently preferred extraocular muscle sensor and stimulator apparatus and method of the present invention will now be described.

Figure 1:
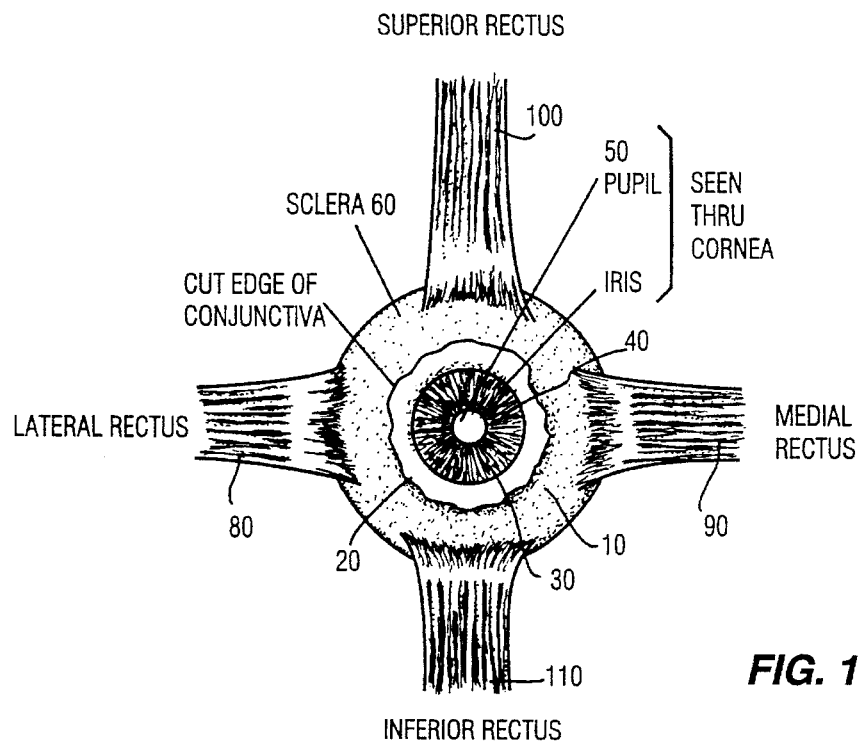
FIG. 1 is a frontal schematic diagram of human eye anatomy which shows the extraocular muscles.
Figure 2:
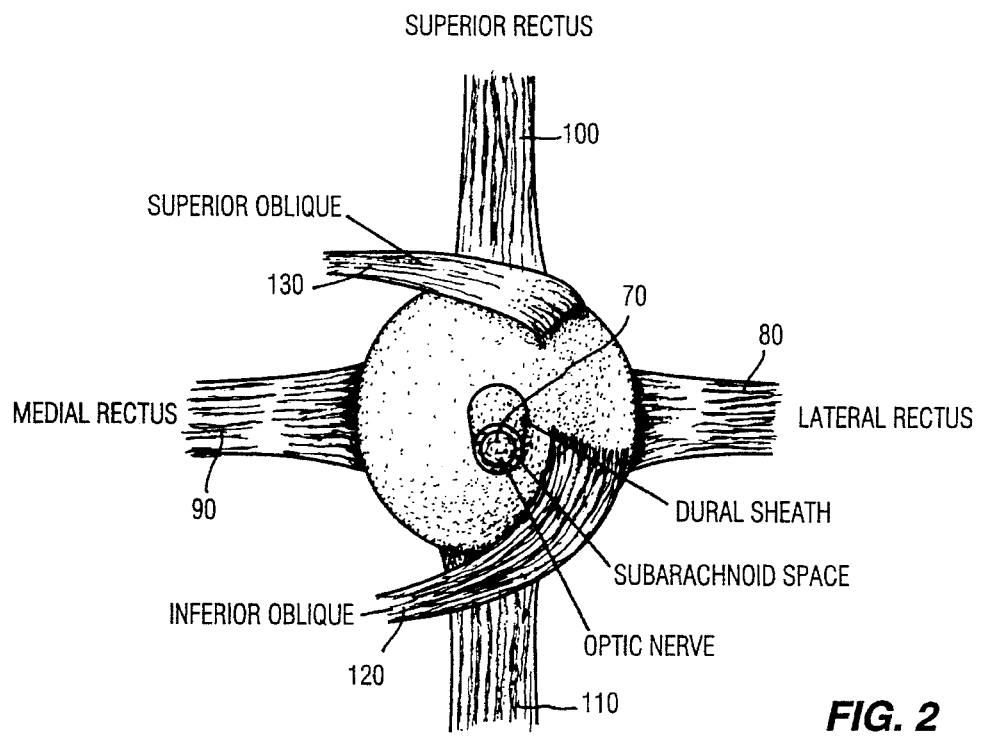
FIG. 2 is a rearward schematic diagram of human eye anatomy which shows the extraocular muscles.

The present invention functions by using four of the twelve extraocular muscles of a patient's eyes 10. Referring to FIGS. 1 and 2, the present invention utilizes both lateral rectus muscles 80 and both medial rectus muscles 90. Specifically, referring to FIG. 3, the present invention utilizes the right lateral rectus muscle 82, the left lateral rectus muscle 83, the right medial rectus muscle 92 and the left medial rectus muscle 93. These muscles 82, 83, 92 and 93 move the patient's eyes 10 together to the left and right in what those skilled in the art refer to as "horizontal vergence movements". For example, in left gaze (looking to the left) the left lateral rectus muscle 83 (referred by those skilled in the art as an "ipsilateral muscle; same side") is activated and the right medial rectus muscle 92 (referred to as a contralateral muscle; opposite side) is activated by the pulsed stimulation from the abducens and oculomotor nerve, respectively. In another example, when the eyes 10 are brought together, which those skilled in the art refer to as "convergence" (which is done when reading, for example), the medial rectus muscles 92 and 93 of both eyes are stimulated simultaneously.

Figure 3:
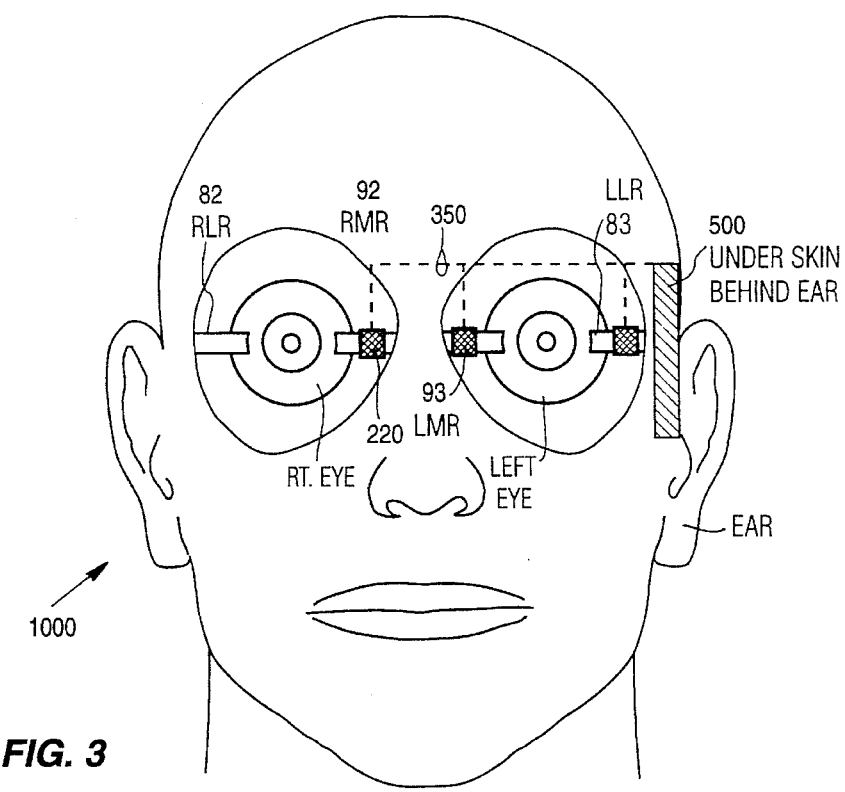
FIG. 3 is a block diagram of the apparatus of the present invention.

FIG. 3 shows a block diagram of an embodiment of an extraocular muscle sensor and stimulator system 1000 of the present invention is shown. This embodiment shows a situation where the left lateral rectus muscle 83 is paralyzed. Those skilled in the art would therefore refer to the muscles of the left eye as "ipsilateral (same side)" and the muscles of the right eye as "contralateral (opposite side)". In this example, left lateral rectus muscle 83 and left medial rectus muscle 93 are therefore "ipsilateral (same side)" and the right lateral rectus muscle 82 and the right medial rectus muscle 92 are therefore contralateral (opposite side).

In the presently preferred embodiment of the present invention, the sensor and stimulator 1000 comprises electrode units 220 implanted on the ipsilateral medal rectus muscle 93 and the contralateral medial rectus muscle 92. These electrodes 220 serve to sense the neuronal inputs to these muscles and transmit the sensed data to the stimulator 500. A similar electrode unit 220 would be placed on the ipsilateral lateral rectus muscle 83. This electrode 220 stimulates this 83 muscle with the output of the stimulator 500.

Electrodes 220 are connected to the stimulator 500 via medical grade implantable insulated conducive wire 250. These wires 250 are passed under the skin (sub-cutaneously) to the unit 500 which in the presently preferred embodiments are located behind the ipsilateral ear or above the clavicle (collar bone).

Figure 4:
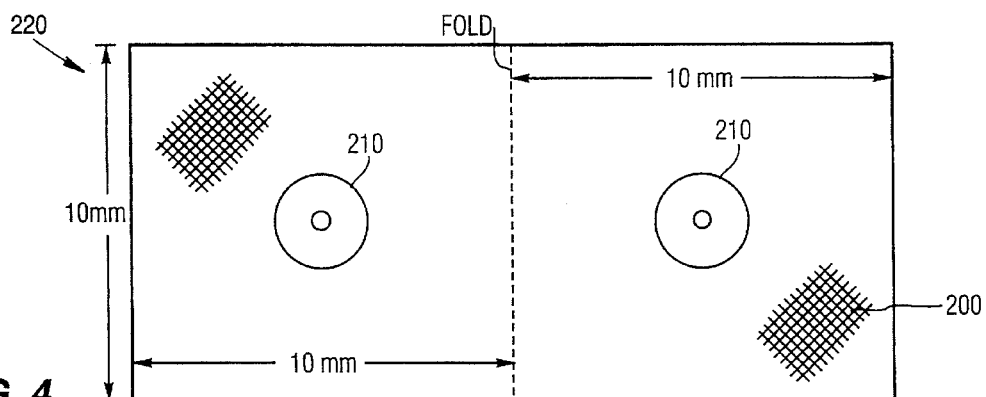
FIG. 4 shows an embodiment of the electrode sensing and stimulating unit of the present invention.

With reference to FIG. 4, the presently preferred design of the implantable electrode units 220 for patient use will now be discussed. The electrodes 220 are preferably constructed of platinum which is connected via a riveting technique to an inert mesh band 200. This mesh band 200 is preferably constructed of medical grade Dacron® mesh. In order to install the electrode units 220, the mesh band 200 containing the electrodes 210, is sutured around the extraocular muscles during a surgical procedure.

The implantation of the proposed device would entail a surgical procedure. The conjunctiva 20 tissue surrounding the eye (see FIGS. 1 and 2) of each eye would be incised and the contralateral medial rectus muscle 92 (opposite side to the paralyzed lateral rectus muscle) would be isolated (i.e., located). After isolating the contralateral medial rectus muscle, an electrode unit 220 is sutured around the muscle. This same electrode unit placement 220 would be carried out for the ipsilateral medial rectus muscle 93 and lateral rectus muscle 83. Medical grade wires 250 contained in a preconstructed wire harness 305 (see FIG. 5) are then passed under the skin of the forehead from the stimulator unit 500 in order to make connections with each electrode units 220. The stimulator unit 500 is placed under skin and muscle in a concealed location such as behind the ipsilateral ear or above the ipsilateral collar bone. Placement of these wires 250 would be done using current surgical techniques well known to those skilled in the art.

Figure 5:
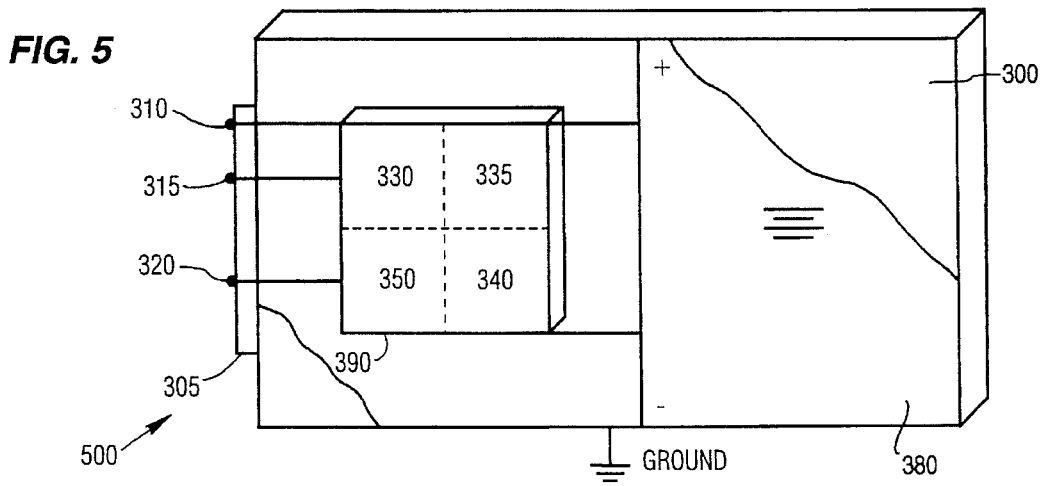
FIG. 5 shows a schematic of an embodiment of the implantable sensor and stimulator of the present invention.

Each electrode unit 220 placed on the medial rectus muscles 90 will sense the neuronal impulses sent to these muscles by the oculomotor nerve (CN III) and communicate this information to the stimulator 500. The stimulator 500 will process this information and generate a signal for transmission to the ipsilateral lateral rectus muscle 83. The stimulator 500 will then transmit this signal to the ipsilateral lateral rectus muscle 83. Without this stimulus which is provided by the present invention, the ipsilateral lateral rectus muscle 83 would receive no stimulus at all. With reference to FIG. 5, the presently preferred stimulator 500 will now be described. The presently preferred stimulator 500 comprises a case 300 that seals the internal components from the unit's 500 external environment and will also serve as the electrical ground. In the presently preferred embodiment, the case 300 is preferably constructed of medical grade, bio-inert stainless steel. A backplane or wiring harness receiver 305 is installed on the exterior of the case 300 which, after installation in a patient, will receive wires 250. Wiring harness receiver 305 has at least three terminals. A first terminal, CMR terminal 310, will be connected to the wire 250 coming from the electrode 220 installed on the contralateral medial rectus 92. Hence, CMR terminal 310 will receive the neuronal impulses sensed by the electrode 220 installed on the contralateral medial rectus 92. A second terminal, IMR terminal 315, will be connected to the wire 250 coming from the electrode 220 installed on the ipsilateral medial rectus 93. Hence, IMR terminal 315 will receive the neuronal impulses sensed by the electrode unit 220 installed on the ipsilateral medial rectus 93. Finally, the third terminal, ILR terminal 320, will be connected to the wire 250 connected to the electrode 220 installed on the ipsilateral lateral rectus 83.

Figures 6A, 6B:
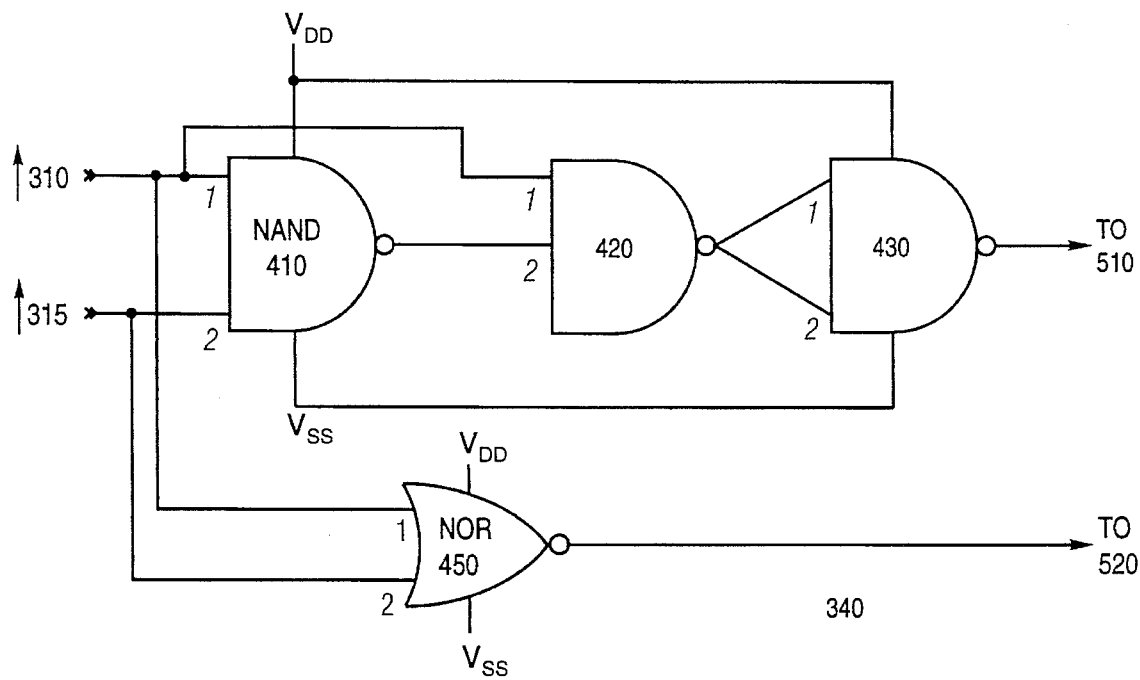
Figure 7:
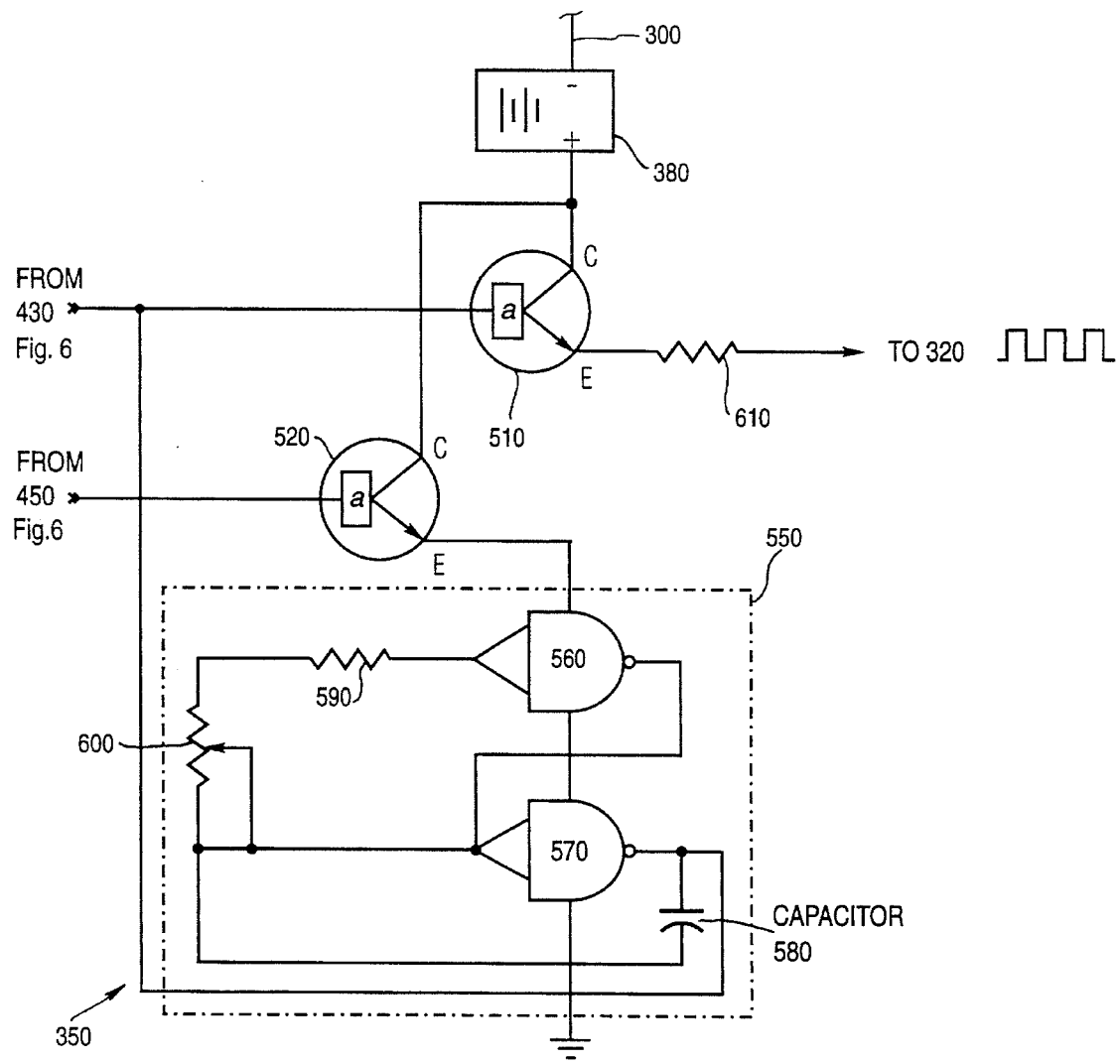
FIG. 7 shows an embodiment of the pulse generator of the present invention.

With reference to FIGS. 5–7, the presently preferred electronic circuitry of stimulator 500 will now be described. All electronics described below can be incorporated on a single integrated circuit 390 fabricated for this purpose. The integrated circuit can be a full custom integrated circuit, a mask programmed gate array or a user-programmable logic device such as a field programmable gate array. All the electronic components, including integrated circuit 390, used in the stimulator 500 receive power from a power supply 380. In the presently preferred embodiment, the power supply is comprised of a lithium battery or similar power supply.

An amplifier 330 is placed in electrical communication with the CMR terminal 310 and IMR terminal 315. During use, amplifier 330 receives the neuronal impulses signals from the CMR terminal 310 and the IMR terminal 315 and amplifies them to levels that are capable of electronic processing. The presently preferred amplifier 330 is a differential operational amplifier. The output of amplifier 330 is presented to a filter 335 that further processes the amplified neuronal impulse signals. The presently preferred filter 335 is comprised of a common-mode rejection circuit along with other noise-suppression electronics. The amplified and conditioned neuronal impulses are then communicated to logic circuit 340.

Using the amplified and conditioned neuronal impulses, the logic circuit 340 generates a signal that is of equal frequency to the neuronal impulses received by the contralateral medial rectus muscle 92. The output from logic circuit 340 is in electrical communication with a pulse generator 350 which will be described below. The signal from pulse generator 350 is sent to the ILR terminal 320, which as discussed, is in electrical communication with wire 250 connected to the electrode 220 installed on the ipsilateral lateral rectus 83. Logic circuit 340 must also assure that no signals are sent to the ILR terminal 320 when both medial rectus muscles 92 and 93 are active, which occurs when the patient performing activities such as reading. Lastly, logic circuit 340 must be capable of providing a tonic stimulation to the ipsilateral lateral rectus 83 when there is no input to either medial rectus muscle. FIG. 6 provides the truth tables for the logic elements used in logic circuit 340.

The structure of logic circuit will now be discussed. Logic circuit 340 is comprised of NAND gate 410. The first input to NAND gate 410 is sourced by the conditioned signal detected from the contralateral medial rectus muscle 92 and received at terminal 310. The second input to NAND gate 410 is sourced by the conditioned signal detected from ipsilateral medal rectus muscle 93 received at terminal 315. The output of NAND gate 410 sources the second input to NAND gate 420. The conditioned signal detected from the contralateral medial rectus muscle 92 sources the first input to NAND gate 420. The output of NAND gate 420 sources both inputs to NAND gate 430. The output of NAND gate 430 sources a first input to pulse generator 350, shown in FIG. 7, for subsequent signal transmission to the ipsilateral lateral rectus muscle 83.

Logic circuit 340 is also comprised of NOR gate 450. The first input to NOR gate 450 is sourced by the conditioned signal detected from the contralateral medial rectus muscle 92 and received at terminal 310. The second input to NOR gate 450 is sourced by the conditioned signal detected from ipsilateral medal rectus muscle 93 received at terminal 315. The output of NOR gate 450 sources a second input to pulse generator 350 for subsequent signal transmission to the ipsilateral lateral rectus muscle 83.

The operation of logic circuit 340 will now be illustrated with reference to FIGS. 6 and 7. The first input to NAND gate 410 is the conditioned signal detected from the contralateral medial rectus muscle 92 and received at terminal 310. The second input to NAND gate 410 is the conditioned signal detected from ipsilateral medal rectus muscle 93. The output of NAND gate 430 should only output a logic "high" when the input received from the contralateral medial rectus muscle 92 is logical "high" and the input received from the ipsilateral medal rectus muscle 93 is logical "low". This situation arises when the patient is performing gaze toward the paralyzed lateral rectus 82, or left gaze. NAND gate 430 should output a logical "low" in all other situations. Logic circuit 340 shown in FIG. 6 provides such a function. If a logical "high" is detected from the contralateral medial rectus muscle 92 and a logical low is detected from the ipsilateral medal rectus muscle 93, NAND gate 410 will output a logical "high". Therefore, the inputs to NAND gate 420 will be the logical "high" from NAND gate 410 and the logical "high" from the contralateral medial rectus muscle 92. Thus, NAND gate 420 will output a logical "low". The output of NAND gate 420 sources both the inputs to NAND gate 430. Since both inputs to NAND gate 430 are logical "low", the output of NAND gate 430 is logical "high". One skilled in the art will recognize that NAND gate 430 will only output a logical "high" if the input received from the contralateral medial rectus muscle 92 is logical "high" and the input received from the ipsilateral medal rectus muscle 93 is logical "low". All other combinations of inputs provide an output of logical "low".

Logic circuit 340, as discussed, also comprises NOR gate 450. NOR gate 450 will only generate an output of logical "high" when neither the contralateral medial rectus muscle 92 nor the ipsilateral medal rectus muscle 93 muscles are receiving input signals. This, as demonstrated in the truth tables of FIG. 6, is because when logical "low" is NORed with logical "low", a logical "high" is generated. This situation arises when the patient is performing distance gaze.

After the logic circuit 340 processes the signals detected from the contralateral medial rectus muscle 92 and the ipsilateral medal rectus muscle 93, the stimulator 500 generates the signal sent to the paralyzed lateral rectus muscle (the ipsilateral lateral rectus muscle 83). In the presently preferred embodiment, pulse generator complex 350, shown in detail in FIG. 7, will control the signals. When the output of NAND gate 430, shown in FIG. 6, is logical "high" it will bias transistor 510 which will emit a pulse determined by the power supply 380 and resistive element 610 to the ILR terminal 320, though wire 250, to the electrode unit 220 on the ipsilateral lateral rectus muscle 83.

The presently preferred pulse generator 350 will also be composed of transistor 520 which will be biased when the output of NOR gate 450 (FIG. 6) is logical "high". When the NOR gate 450 outputs a "high", transistor 520 will be biased and activate emit a signal which will be transmitted to the tonic pulse circuit 550. The presently preferred tonic pulse circuit 550 is composed of NAND gates 560 and 570, resistor 590, variable resistor 600 and capacitor 580. The resistance and capacitance of resistor 590, variable resistor 600 and capacitor 580 are selected to provide the proper frequency for a tonic baseline pulse to be generated. Fine tuning of the tonic pulse circuit 550 is accomplished via the variable resistive element 600. In the presently preferred embodiment, resistive element 600 can be externally controlled after implantation of device 500. This tonic pulse circuit 550 will provide a signal to the ipsilateral lateral rectus muscle 83 when both medial rectus muscles 92 and 93 are inactive as in distance vision. This tonic pulse will be varied by the variable resistor 600 and may be controlled externally through methods known to those skilled in the art. The output of the tonic pulse circuit 550, which will be a square wave, is connected to the base of transistor 510. Transistor 510 will then stimulate the ipsilateral lateral rectus muscle 83 in the manner discussed above.

In summary, two muscles are involved in lateral gaze, the ipsilateral lateral rectus muscle 83 and the contralateral medial rectus muscle 92. In the situation of a paralyzed lateral rectus muscle, the contralateral medial rectus is the only functioning muscle of the pair involved in lateral gaze. By sensing the neuronal impulse signals from the contralateral medial rectus muscle (reference numeral 92 in the current example), and providing a signal matching the frequency and magnitude of those neuronal impulse signals to the ipsilateral lateral rectus muscle (reference numeral 83 in the current example) reestablishment of the paralyzed lateral rectus muscle function is possible. The sensor 220 on the ipsilateral medial rectus muscle 93 serves to sense for convergence movement, which allows the present invention to determine when the patient is performing activities such as reading. In this situation, the logic circuit prevents firing of the left lateral rectus 83 muscle when the contralateral right medial rectus muscle 92 was involved in convergence and not lateral gaze.

One skilled in the art will recognize that the above discussion of the present invention is for the situation of a paralyzed left lateral rectus, as shown in FIG. 3. The concepts of the present invention are equally applicable to the situation of a paralyzed right lateral rectus. The only difference is that the electrode units 220 will be installed in the opposite eyes. Thus, the present invention is equally applicable to paralysis of a right or left lateral rectus.

In the presently preferred embodiment, the stimulator 500 is surgically implanted behind one of the patient's ears, for example behind the ipsilateral ear, such that it is buried under the skin and muscle of the scalp. This location would provide ease of access for service and would be cosmetically acceptable. Wires 250 are installed such that they travel subcutaneously (under the skin). Those wires 250 are connected to electrode units 220 previously installed on the muscles described above. The wires 250 would be contained in a common harness (not shown), insulated from each other and would travel under the forehead skin and muscle and drop down to the respective orbits and return to the stimulator unit 500.

In order to aid in the understanding the present invention, the following example of a paralyzed left lateral rectus 83 is provided. As discussed, a patient with a paralyzed left lateral rectus 83 would be incapable of gaze to the left without double vision. This patient would therefore maintain her head turned to the left in order to avoid use of the paretic muscle 83. In a patient having the present invention installed therein, electrode units 220 would be installed in the left medial rectus muscle 93, the right medial rectus muscle 92 and left lateral rectus muscle 83. The present invention would sense the neuronal impulse signals received by the right and left medial rectus muscles 92 and 93 via the electrode units 220. The neuronal impulse signals sent to the right and left medial rectus muscles 92 and 93, in addition to controlling those muscles, would be transmitted to the stimulator 500 via wire 250. These neuronal impulse signals are then amplified by amplifier 330 and conditioned by filter 335. These conditioned signals are then processed by the logic circuit 340, which would determine when the right medial rectus muscle 92 was firing and the left medial rectus muscle 93 was not and send a pulse via pulse generator 350 of frequency equal to that of the right medial rectus muscle 92 to the paralyzed left lateral rectus muscle 83. The logic circuit functions in this way to produce a pulse to the left lateral rectus muscle 83 only when the right medial rectus muscle 92 is active alone, such as when the patient is performing left gaze. Furthermore, this logic circuit 340 would prevent the generation of a pulse when the eyes were converging and would provide a tonic stimulation to the paralyzed left lateral rectus muscle 83 when neither the right or left medial rectus muscle 92 and 93 was acting.

A preferred method and apparatus for extraocular muscle sensing and stimulation has been described. While embodiments and applications of this invention have been shown and described, as would be apparent to those skilled in the art, many more embodiments and applications are possible without departing from the inventive concepts disclosed herein. The invention is consequently not to be restricted except in the spirit of the appended claims.

What is claimed is:

1. In a patient having a first eye and a second eye, an apparatus for stimulating a paralyzed or non-inervated lateral rectus muscle of the first eye, the first eye moved by an ipsilateral lateral rectus muscle and an ipsilateral medial rectus muscle and the second eye moved by a contralateral medial rectus muscle and a contralateral lateral rectus muscle, the apparatus comprising:

a first electrode adapted to be installed in the ipsilateral lateral rectus muscle;

a second electrode adapted to be installed in the ipsilateral medial rectus muscle;

a third electrode adapted to be installed in the contralateral medial rectus muscle; and a control unit, said control unit in electrical communication with said first electrode, said second electrode and said third electrode, said control unit providing a stimulation signal to said first electrode of equal magnitude and frequency of neuronal impulses received by the contralateral medial rectus and detected by said third electrode when neuronal impulses are received by said third electrode but not said second electrode, said control unit further providing an electrical impulse of predetermined magnitude and frequency to said first electrode when no neuronal impulses are detected by said second and said third electrodes.

* * * * *